(12) United States Patent
Eghtesady

(10) Patent No.: US 7,709,210 B2
(45) Date of Patent: May 4, 2010

(54) DIAGNOSIS AND PREVENTION OF FETAL HEART DISEASE

(75) Inventor: Pirooz Eghtesady, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 301 days.

(21) Appl. No.: 11/538,527

(22) Filed: Oct. 4, 2006

(65) Prior Publication Data

US 2007/0105168 A1 May 10, 2007

Related U.S. Application Data

(60) Provisional application No. 60/723,742, filed on Oct. 5, 2005.

(51) Int. Cl.
*G01N 33/53* (2006.01)
(52) U.S. Cl. .................. 435/7.1; 435/7.34; 435/7.9; 435/7.94; 435/29; 435/975; 435/253.4; 435/961; 530/388.4; 530/389.5; 530/391.1; 530/391.3
(58) Field of Classification Search .................. 435/7.1, 435/7.34, 7.9, 7.94, 29, 259, 975, 961, 253.4; 530/388.4, 389.5, 391.1, 391.3
See application file for complete search history.

(56) References Cited

U.S. PATENT DOCUMENTS

| | | | | |
|---|---|---|---|---|
| 3,699,003 | A * | 10/1972 | Kronish et al. ................. | 435/36 |
| 5,098,827 | A * | 3/1992 | Boyle et al. ................. | 435/7.34 |
| 2008/0183092 | A1* | 7/2008 | Smith et al. ................. | 600/511 |

FOREIGN PATENT DOCUMENTS

| WO | WO 91/08304 | * | 6/1991 |
|---|---|---|---|
| WO | WO 9108304 | * | 6/1991 |

OTHER PUBLICATIONS

Fischer et al., Intravenous Immunoglobulin in Neonatal Group B Streptococcal Disease. The American Journal of Medicine. Mar. 1984. vol. 76. No. 3A. pp. 117-123.*
Lim et al., Reduction of Morbidity and Mortality Rates for Neonatal Group B Streptococcal Disease through Early Diagnosis and Chemoprophylaxis. Journal of Clinical Microbiology. Mar. 1986. vol. 23, No. 3. pp. 489-492.*
Tanaka et al., Successful Treatment of Both Mother and Infact in Pregnancy-Associated Group A Streptococcal Toxic Shock Syndrome. American Journal of Infectious Diseases. 2007. vol. 3, No. 1 pp. 1-6.*
Trivier et al., Path. Biol. vol. 47, No. 8. pp. 784-789. 1999.*
Revised Guidelines for Prevention of Early-onset Group B Streptococcal (GBS) Infection. American Academy of Pediatrics. Pediatrics. vol. 99, No. 3. Mar. 1997. pp. 489-496.*
Hughes et al., International Journal of Cardiology. vol. 18. 1988. pp. 261-262.*
Corneli, C. "Rapid detection and diagnosis of group A Streptococcal pharyngitis." Current Infectious Disease Reports 2004, 6: 181-186.
Cunningham, M. "Pathogenesis of group A Streptococcal infections." Clinical Microbiology Reviews, Jul. 2000: 470-511.
Sheeler, R. "Accuracy of rapid Strep testing in patients who have had recent Streptococcal pharyngitis." J Am Board Fam Pract 2002, 15:261-265.
Julene S. Carvalho, "Fetal Heart Scanning in the First Trimester", Prenat Diagn 2004; 24: 1060-1067 Published online in Wiley InterScience (w.w.w..interscience.wiley.com).
Jing Deng et al, "New Fetal Cardiac Imaging Techniques", Prenat Diagn 2004; 24: 1092-1103.
H.M. Gardiner, "Fetal Echocardiography: 20 Years of Progress", Heart 2001; 86; 12-22.
"Accuracy of Fetal Echocardiography in the Routine Detection of Congenital Heart Disease Among Unselected and Low Risk Populations: A Systematic Review"—BJOG—Jan. 2005, vol. 112, pp. 24-30.

* cited by examiner

*Primary Examiner*—Bao-Thuy L Nguyen
(74) *Attorney, Agent, or Firm*—Frost Brown Todd LLC

(57) ABSTRACT

The present invention relates to a method for assessing the likelihood of the presence or formation of fetal heart disease (such as HLHS) in a fetus. In this methodology, the mother, either before or during pregnancy, is tested for the presence of anti-strep antibodies. If positive, the fetus is evaluated and monitored for the presence of fetal heart disease; the fetus can be treated, if appropriate. In addition, either prior to pregnancy or during the first trimester, the mother can be treated to prevent the formation of such antibodies or to neutralize their presence or effect fetal heart tissue.

3 Claims, No Drawings

DIAGNOSIS AND PREVENTION OF FETAL HEART DISEASE

CROSS REFERENCE TO RELATED APPLICATION

This application is related to and claims priority from U.S. Provisional Patent Application No. 60/723,742, Eghtesady, filed Oct. 5, 2005, incorporated herein by reference.

BACKGROUND OF THE INVENTION

The present invention relates to a methodology for assessing the likelihood that a fetus will be at enhanced risk to develop fetal heart disease. The methodology utilizes maternal testing for an antecedent streptococcal infection. The invention also encompasses a method for preventing the formation of such heart disease.

Hypoplastic left heart syndrome (HLHS) and its variants (including aortic stenosis and mitral stenosis) are severe congenital heart defects with substantial associated morbidity and mortality. The primary disease process involves damage and underdevelopment of the left-side heart structures such that the end result is an abnormal heart not capable of supporting the normal circulation of a newborn. Treatment currently entails either high risk and costly multistage reconstructive surgery or heart transplantation, all commencing immediately after birth. These left-side heart structure defects, as well as similar right-side heart structure defects, are collectively referred to herein as "fetal heart disease."

The etiology of this and associated conditions is not currently known. A genetic etiology has been proposed based on limited familial occurrence, but no genetic mutation has been attributed to this disease or its variants. Indeed, HLHS and associated conditions have been linked to nearly every single chromosomal and syndromic anomaly. Although less common, congenital heart defects affecting the right-side of the heart result in similar underdevelopments of the right-side heart structures (such as pulmonary stenosis or pulmonary atresia or tricuspid valve stenosis). This can also result in disabling heart disease of the newborn and, similar to the previously discussed defects, their etiology remains unknown. It would be a very positive development to understand the etiology of fetal heart disease so that a given fetus's predisposition to such condition could be evaluated and, if the predisposition is high, appropriate palliative measures can be taken, perhaps while the fetus is still in utero.

SUMMARY OF THE INVENTION

The present invention, therefore, relates to a method for assessing the likelihood of the presence or formation of fetal heart disease (such as HLHS) in a fetus, comprising testing for the presence of anti-strep antibodies (group A, C or G) in a woman pregnant with said fetus, said woman being asymptomatic for a strep infection at the time of the test. If the testing is positive for the presence of strep A antibodies, then the fetus is evaluated and monitored for the presence of HLHS or other fetal heart disease. Alternatively, the fetus can be treated through either treatment of the mother for an asymptomatic strep infection or through immunologic treatment of either the mother, fetus or both, for example, with such agents as intravenous immunoglobulin (IVIG).

The present invention also relates to a method for assessing the likelihood of presence or formation of fetal heart disease (such as HLHS) in a fetus, comprising testing for the presence of anti-strep antibodies in a woman pregnant with said fetus and, if positive, evaluating and monitoring said fetus for the presence of fetal heart disease.

Finally, the present invention relates to a method for preventing the formation of fetal heart disease (such as HLHS), comprising testing for the presence of anti-strep antibodies in a woman who is not pregnant and, if the testing is positive, treating for the presence of anti-strep antibodies in said woman prior to her becoming pregnant or within the first trimester of her pregnancy.

DETAILED DESCRIPTION OF THE INVENTION

The crux of the present invention is the concept that the pathogenesis of fetal heart disease, as described above, is related to an immunologic injury to the fetal heart during development from a group of maternal antibodies that cross the placenta during gestation. These antibodies were generated in the mother previously in response to an antecedent streptococcal infection, most likely of a pharyngeal location. In the mother, the previous infection (for example, "strep throat") would lead to development of the antibodies that were originally designed to destroy the bacteria responsible for the step throat, the group A beta-hemolytic streptococcus, or the group C and G beta-hemolytic streptococcus. As used herein, the phrase "anti-strep antibodies" is intended to encompass the Group A, C or G antibodies, as well as any other antibodies which form in the mother in response to a strep infection. By chance, these antibodies have the potential to cross-react with fetal heart tissue, particularly in a male fetus. The resulting injury to the cardiac valves and heart muscle leads secondarily to abnormal blood flow through the left-side heart structures, causing the observed pathologies.

The concept of strep throat infection leading to heart disease has some precedent; it the cornerstone of the rationale for treatment to prevent rheumatic heart disease and fever in children and adults. However, the concept that such an event could be participating in the pathogenesis of fetal heart disease has never been put forward previously. In rheumatic heart disease, for unknown reasons, the predominant disease process involves the left-side heart structures, the right-side (or both sides) involvement of the heart has also been reported. The present inventor believes that the same predisposition in the fetus explains the preponderance of left-side fetal heart disease and the less frequent right-side heart disease. Further, there is precedent for transplacental injury to the fetus via an immunologic mechanism as seen in congenital heart block or fetal thrombocytopenia and associated fetal loss.

It is proposed herein that unlike current popular thinking (genetic etiology), these fetal heart diseases and perhaps even the common bicuspid aortic valve, the primary source of aortic stenosis that ultimately affects the adult population, and coarctation of the aorta, are manifestations of the same disease process. This would suggest that a significant portion of heart disease affecting the population may in fact be attributed to such an early mechanism that may continue into adulthood through subsequent repeated exposure of the individual to the streptococcus species.

Thus, in executing the method of the present invention, a test for the presence of strep antibodies and strep infection may be administered to a woman who is not, at the time of the test, symptomatic for a strep infection. Such tests are known in the art. For example, Cunningham, Clin. Microbiol. Rev. 13: 470-511 (2000) describes the standard throat culture procedure. Further, Corneli, Curr. Infect. Dis. Rep. 6: 181-186 (2004), and Sheeler, et al, J. Am. Board Fam. Prac. 15: 261-265 (2002) discuss the rapid antigen testing technique and compare it to throat cultures. The woman who is tested may be pregnant at the time of the test (for determining the risk of fetal heart disease to that particular fetus), or may not be pregnant (for the purpose of assessing the risk of fetal heart disease to fetuses of future pregnancies). If the woman is pregnant and the strep tests are positive, then the fetus can be evaluated and monitored for the presence or development of fetal heart disease, such as HLHS. If interested, the pregnant women can be treated with antibiotics to diminish the risk of developing a fetus with affected heart disease (preventive therapy). If fetal heart disease is present in the fetus, then appropriate treatment techniques can be utilized to mitigate the condition, including such immunologic therapy as administration of IVIG (or a more specifically-targeted material), steroids, and immune system modulators to the mother, fetus or both. Alternatively, a mechanism to clear the placental circulation of these antibodies, for example through plasmapheresis of either mother or fetus, may help mitigate continuing injury to the fetal heart. Other treatment approaches could include a Strep vaccine developed and used with the purpose of being given to women of reproductive age. Similarly, antibodies or reagents could be developed that would function by interfering with the passage of antibodies across the placenta or with the interaction of the antibodies with fetal heart tissue antigens. Blood or amniotic fluid samples from the fetus may also be tested for presence of these anti-strep antibodies to further confirm presence or absence of disease or for assessing the effects and adequacy of any therapy on the baby. If the woman is not pregnant, then appropriate treatment can be administered prior to her next pregnancy or during the early part of that pregnancy (e.g., the first trimester).

The implications of the present invention include the fact that attributable heart defects may be preventable through screening of pregnant mothers for the presence of streptococcal infection or a carrier state for strep antibodies. Further, development of vaccines for strep could then be applied to this particular population or others at risk to prevent the development or progression of various heart diseases. Further, the treatment of these heart defects may be feasible in utero through implementation of IVIG, antibiotics, plasmapheresis or alternative immunologic therapy, or a combination thereof. Simultaneously, a similar protocol may be combined with more invasive fetal therapeutic measures (such as catheter intervention) to achieve successful prenatal therapy. The present invention would allow for the identification of mothers potentially at risk for giving birth to children with fetal heart disease. This would allow for early intervention, or perhaps even therapy, through antibody therapies that would interfere with the pathogenic antibodies, thereby reducing the risk of fetal heart conditions in an existing pregnancy or future pregnancies.

What is claimed is:

1. A method for assessing whether a fetus should be tested for heart disease, comprising testing for the presence of anti-strep antibodies of group A, C or G in a pregnant woman asymptomatic for strep infection at the time of said test and, if said test is positive for the presence of those anti-strep antibodies, of evaluating and monitoring the fetus for the presence of fetal heart disease.

2. The method according to claim 1 wherein the fetal heart disease is characterized by damage to the left-hand heart structures.

3. The method according to claim 2 wherein the fetal heart disease is HLHS.

* * * * *